United States Patent [19]
Apkarian et al.

[11] Patent Number: 6,018,675
[45] Date of Patent: Jan. 25, 2000

[54] ASSEMBLY AND METHOD FOR OBJECTIVELY MEASURING PAIN IN A SUBJECT

[75] Inventors: A. Vania Apkarian, Syracuse; Nikolaus M. Szeverenyi, Lafayette, both of N.Y.

[73] Assignee: The Research Foundation of State University of New York, Albany, N.Y.

[21] Appl. No.: 09/082,992

[22] Filed: May 22, 1998

[51] Int. Cl.[7] ........................................ A61B 5/00
[52] U.S. Cl. ...................... 600/407; 600/410; 600/425; 600/555; 600/557
[58] Field of Search .................... 600/407, 410, 600/411, 425, 427, 555, 557, 554

[56] References Cited

U.S. PATENT DOCUMENTS

| | | | |
|---|---|---|---|
| 5,220,921 | 6/1993 | Ferris et al. | 600/557 |
| 5,533,514 | 7/1996 | Lavigne et al. | 600/557 |
| 5,732,702 | 3/1998 | Mueller | 600/410 |
| 5,806,522 | 9/1998 | Katims | 600/557 |

*Primary Examiner*—Ruth S. Smith
*Attorney, Agent, or Firm*—McAulay Nissen Goldberg Kiel & Hand, LLC

[57] ABSTRACT

A device and methodology is disclosed for the objective measurement of pain in awake human subjects. A variable intensity painful stimulus is given to the subject in a time dependent manner, the patient's brain responses are recorded using an appropriate imaging modality (e.g. functional MR) while the subject indicates the level of discomfort using a "perceptometer" or other similar pain rating device. The pain rating is correlated with the imaging results using a quantitative analysis to characterize the brain's representation of this pain. Color overlays are generated on high resolution anatomical images (MR or other modality) of the brain summarizing the calculated pain related analysis information.

15 Claims, 4 Drawing Sheets

ASSEMBLY AND METHOD FOR OBJECTIVELY MEASURING PAIN IN A SUBJECT

This invention was made with government support under Contract 5R01NS3511502 awarded by National Institute of Neurological Disorders and Stroke. The government has certain lights in the invention.

This invention relates to an assembly and method of objectively measuring pain in a subject.

Pain, being a subjective experience, is a difficult affliction to measure in an objective manner. Further, the existence of a chronic pain state in a patient can be very difficult to determine since such a state is one not readily modulated and is a subjective perception. It is also known that the chronic pain state in individuals has been extremely costly in terms of health care and lost revenues. In general, there are no drug treatments effective for a long-term control of a chronic pain state.

Over the years, various attempts have been made to analyze the degree of pain in a subject. For example, there has been a large increase in the use of brain imaging technologies to study pain. Some of these brain imaging technologies are discussed in Apkarian, V. A., Functional Imaging of Pain: New Insights Regarding the Role of the Cerebral Cortex in Human Pain Perception, Seminars in The Neurosciences, Vol. 7, 1995: pp279–293.

Simply stated, brain imaging technologies are able to image a section of a brain (or the whole brain) which responds to a pain stimulus with a succession of such images being obtained for different levels of the stimulus. All earlier studies use the timing of the stimulus (as well as its intensity) to separate the brain images into different groupings for statistical analyses. This procedure is appropriate as long as the stimulus and the associated perception are tightly time locked, which is the usual situation in normal subjects. However, in patients with abnormal pain perceptions, often the presentation of a stimulus and the perception of pain may not be properly time related. The same stimulus in one type of pain patient may result in severe pain that continues long past the end of the stimulus; while in other patients the same stimulus may not result in pain perception at all. Therefore, analyzing the brain images in relation to the stimulus becomes inappropriate in pain patients and can give rise to misleading results. Thus, in pain patients in general and even in normal subjects under specific stimulus conditions, the imaging data which is obtained is incomplete in providing an objective measurement of pain. For the brain activity obtained in these conditions, although related to the stimulus, it does not reflect the proper episodes where the subject did or did not feel pain, or the episodes where the pain was increased or decreased. Instead, there is a need to show changes in pain perception that better corresponds to the subjects' own perceptions, which can then be related to the brain activity. Such an approach in turn enables an accurate assessment of brain activity changes with pain, providing an objective measure of pain perception.

Accordingly, it is an object of the invention to provide a technique for objectively measuring changes in pain.

It is another object of the invention to be able to evaluate the presence of chronic pain in a patient.

Briefly, the invention is directed to an assembly and method for objectively measuring pain in a subject.

The assembly includes an imaging device for recording and imaging a sequence of brain responses of a subject, e.g. a human patient, to a variable painful stimulus over a period of time and for emitting a trigger signal in response to each imaged brain response. Such an imaging device may be a functional magnetic resonance imaging device (fMRI) or any other type of functional monitoring modality, such as computed tomography (CT), electro-encephalography (EEG), cortical evoked potentials (CEP), near infra-red spectroscopy (near IRS) and magneto-encephalography (MEG).

The assembly also includes a subject controlled pain rating device which is controlled by the subject to emit a signal corresponding to a subject-perceived level of discomfort during the time that the variable painful stimulus is applied to the subject.

The assembly also includes a computer interface for correlating each of the sequence of recorded brain responses to the signals corresponding to the levels of discomfort in dependence on the trigger signal. The computer interface serves to not only provide information with respect to the effect of the variable painful stimulus on a selected area of a brain over time but also has this information correlated to the levels of discomfort experienced by the subject.

In accordance with one particular embodiment of the invention, an assembly is provided for measuring changes in pain which includes an imaging device for recording and imaging a sequence of brain images of a subject over a time period and emitting a trigger signal in response to each imaged brain response, a first computer for collecting the sequence of brain images from the imaging device and emitting information corresponding thereto, a first means for applying a variable painful stimulus to the subject during the time period, a pain rating device for indicating levels of discomfort of the subject to the various painful stimulus and a second computer operatively connected to the means for applying the stimulus to vary the stimulus at selected times and for emitting information corresponding thereto. This second computer is also connected to the imaging device to receive the trigger signals. Still further, this assembly includes a data analysis computer for receiving the information emitted from the first computer and the information emitted from the second computer in order to produce a record correlating changes in the brain images in response to changes in the stimulus relative to indicated levels of discomfort.

The invention also provides a method of objectively measuring pain which includes the steps of applying a variable painful stimulus to a subject in a time dependent manner, objectively imaging brain responses of the subject during application of the stimulus, recording subjective indications of the level of discomfort of the subject during application of the stimulus and correlating the subjective indications of the level of discomfort with the objectively imaged brain responses in order to characterize the brain's representation of the perception that the subject experiences.

With this method, a high resolution anatomical image of the brain of the subject may be generated and color overlays may be positioned on the anatomical image to provide a summary of calculated brain analysis information.

Simply stated, during an examination, the subject is subjected to a variable pain over a period of time during which brain responses of the subject are objectively imaged and during which time subjective indications of the level of discomfort of the subject are recorded. Thereafter, the subjective indications of the level of discomfort are correlated with the objectively imaged brain responses in order to characterize the brain's representation of the pain in relation to the subject's perception and irrespective of the details of the stimulus, which may be only weakly related to the perception. In this method, the subject may be externally manipulated in order to inflict a variable pain. Such manipulation may include the movement of a leg in the case of a subject experiencing chronic back pain. In other cases, the variable pain, may be provided by the application of an external stimulus such as a thermal stimulus. In all cases, the stimulus only provides a means for perturbing the subject's pain perception, but the subject himself/herself provides the perception signal used for analyzing the brain images.

The invention is particularly useful in establishing whether or not a patient has an existing pain condition. In this respect, a large number of patients having the same pain-causing condition are tested using the above techniques in order to obtain an "aggregate" value for the condition. This, sampling of patients may also include patients who do not have the pain condition to test the reliability of the results obtained. For example, in order to establish an "aggregate" value of the brain images to be expected for a patient having a lower back pain condition, several patients are tested to obtain brain images for different levels of pain inflicted on the patients, for example, by raising a patient's leg to different angles to the horizontal. That is to say, with a patient placed in a supine position, each leg of the patient can be raised to different angles to the horizontal, for example, in 5° increments. The brain images which are taken for each angular increment are then correlated with the pain rating indicated by the patient. The resultant brain images relative to an indicated pain level may then be aggregated for these patients in order to establish an "aggregate" value to be expected for different levels of pain indicated by the rating device.

Once the "aggregate" value has been established, a subject patient may be subjected to a similar protocol to obtain the patient's rating of pain for each angular increment of the patient's leg relative to the horizontal. The brain image of the patient corresponding to the pain rating can then be compared to the aggregate brain image to be expected for the given pain rating. Deviations of the actual brain image from the expected aggregate brain image can then be used as objective evidence of feigned pain.

For example, if the brain images of the "aggregate" indicates modest brain activity (i.e. tracings) for a minor level of pain but the patient in question having a similar brain image rates the pain as excruciating, this may be an objective holding that the patient, as compared to the protocol, in all likelihood does not actually have an excruciating pain.

The invention may also be used in cases where a subject is suspected of reporting pain fraudulently. In these cases, the brain images should not show any pain activity since the subject, although indicating the presence of pain with the pain rating device, does not have the proper perception. Comparing the brain activity in such cases to "aggregates" where subjects without pain "pretend its presence" during scanning would clarify whether the subject is being fraudulent or not.

These and other objects and advantages of the invention will become more apparent from the following detailed description taken in conjunction with the accompanying drawings wherein:

FIG. 1 schematically illustrates an assembly for measuring pain in a subject;

FIG. 2 graphically illustrates a correlation between the application of a stimulus over time, a subjective determination of the levels of discomfort due to the stimulus over the same time and a sequence of brain images obtained over the same time in relation to the stimulus;

Figure 1:
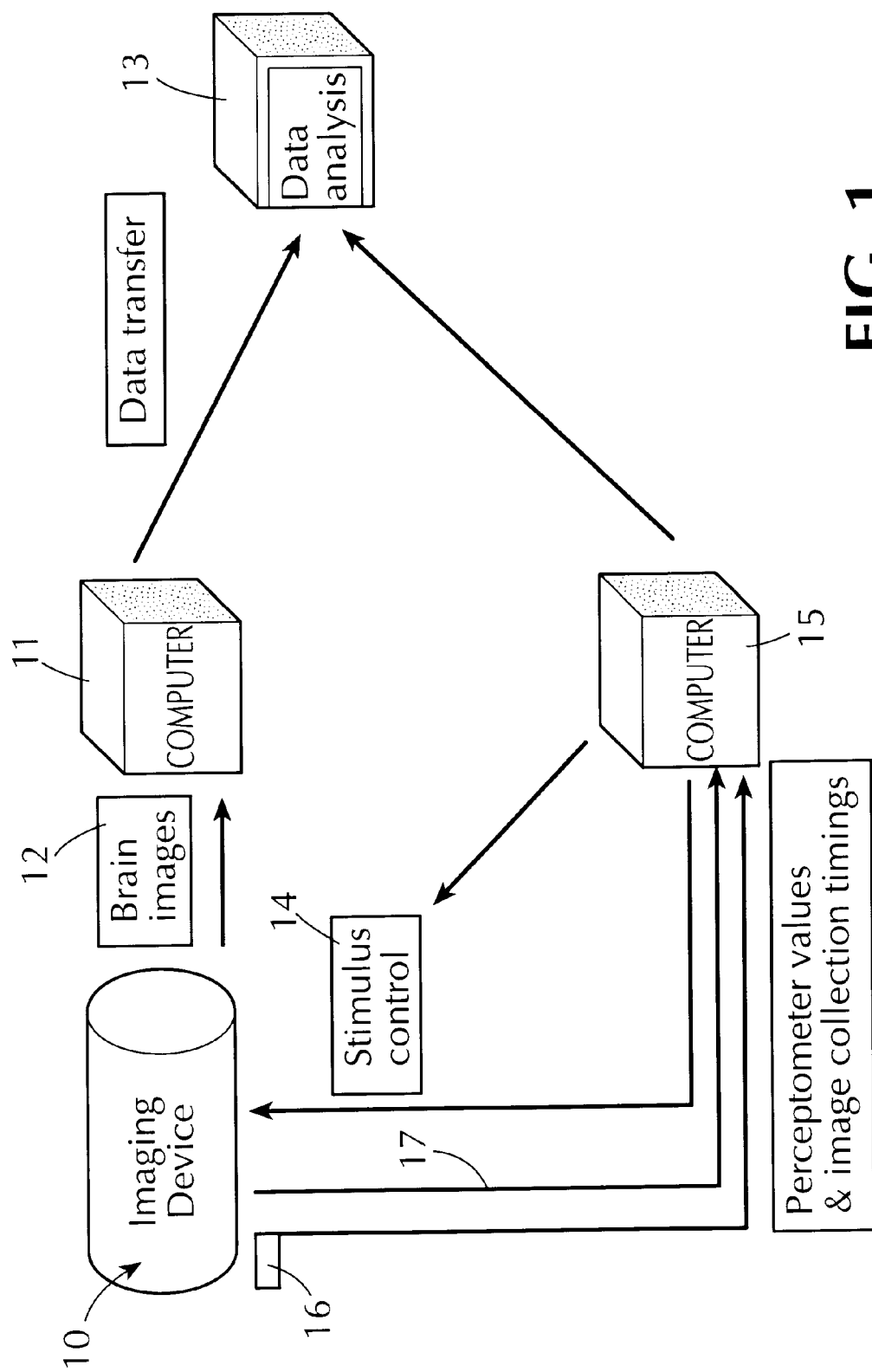

Referring to FIG. 1, the assembly for objectively measuring pain includes an imaging device 10 for recording and imaging a sequence of brain images of a subject over a time period. This imaging device 10 may be in the form of a functional magnetic resonance imaging device (fMRI) e.g. a 1.5 Tesla G.E. equipped with Echo Planar Imaging (EPI). This imaging device allows a non-invasive evaluation of brain activity patterns in a variety of situations and can be used as a monitor of pain perception in a subject if the pain state is varied and known during an examination.

The imaging device 10 is operatively connected with a computer 11 which serves to collect a sequence of brain images 12 from the imaging device 10 and for emitting information corresponding thereto, for example, to a data analysis computer 13.

The assembly also includes a means 14 for applying a variable pain-inducing stimulus to a subject in the imaging device 10 over the time period of examination. This means 14 may be of the type which applies a thermal stimulus as is known. Currently, this means 14 is controlled by a personal computer 15 running Windows 95 with LabView software used to control the timing and intensity of the stimulus.

The assembly also includes a pain rating device 16 for subjectively indicating levels of discomfort of the subject to the variable painful stimulus over the examination time period. This pain rating device 16 is operatively connected to the computer 15 in order to have the computer 15 record the changes in the levels of discomfort and to emit information corresponding thereto to the data analysis computer 13. The subject-controlled rating device 16 that logs the ongoing subject's feeling and the operatively connected computer 15 serve as a "perceptometer". This information is collected using the same LabView software which also controls the stimulus.

The imaging device 10 also emits a trigger signal 17 to the computer 15 which is indicative of the exact timing during which every specific brain image is collected. This trigger signal 17 together with the "perceptometer" value, read exactly at the same time, are the signals necessary for appropriately analyzing the brain images.

During operation, a subject such as a chronic back pain patient is placed within the imaging device 10 and provided with a pain rating device 16 to be manipulated during an examination time period. For example, the subject is placed within a ring magnet (not shown) of a MRI machine for scanning during the examination with one hand having access to the pain rating device 16. Thereafter, a stimulus is applied to the subject in order to effect pain. This pain is then recorded as a sequence of images 12 of brain activity of the part of the brain reacting to the stimulus of the subject via the imaging device 10 and, at the same time, the subject subjectively indicates the level of pain via the pain rating device 16. These brain images 12 are then transmitted to the computer 11 that controls where the images are taken in a brain and collects the brain images for transfer to the data analysis computer 13. At the same time, the other computer 15 is used to control the subject's stimulation and to collect the trigger signals 17 indicative of the timings of the brain images as well as the information received from the subject-controlled rating device 16. This information is also emitted to the data analysis computer 13 and the data from both computers 11, 15 are combined to determine brain activity.

Figure 2:
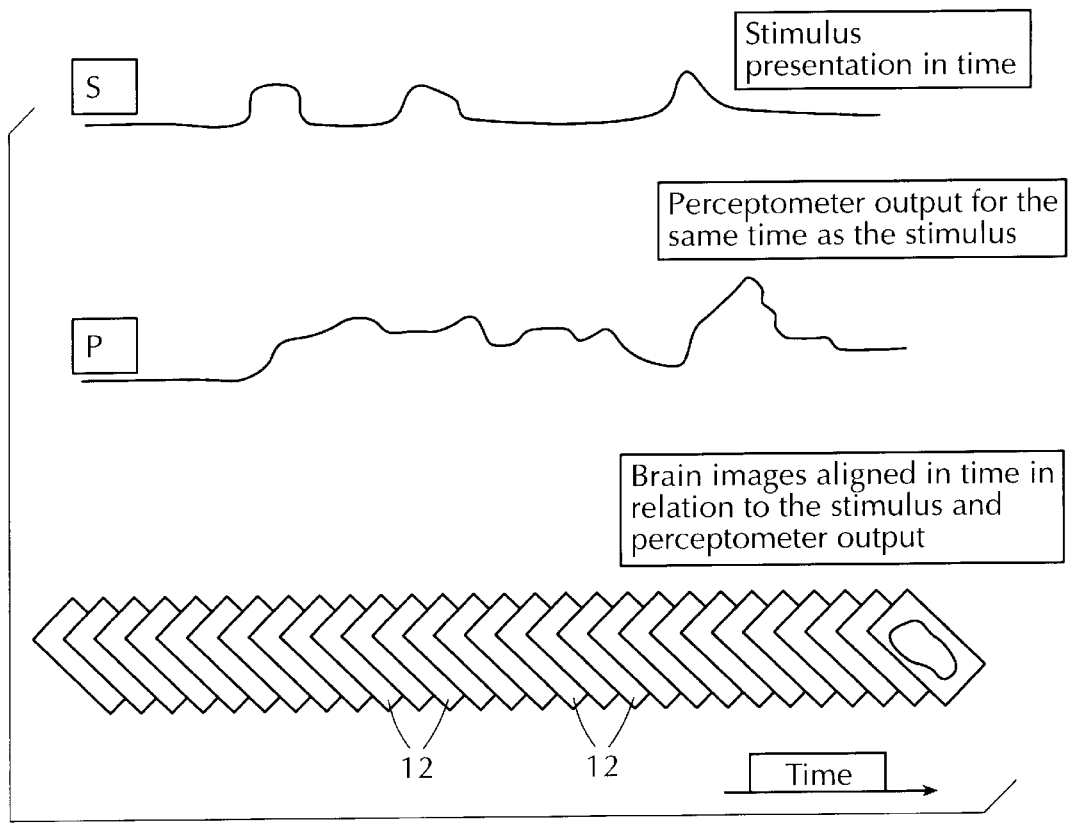

FIG. 2 graphically illustrates a relationship between the stimulus (S) presentation in time relative to the perceptometer (P) output for the same time as the stimulus (S). In addition, FIG. 2 graphically illustrates a sequence of brain images 12 aligned in time in relation to the stimulus (S) and perceptometer (P) output.

Figure 3:
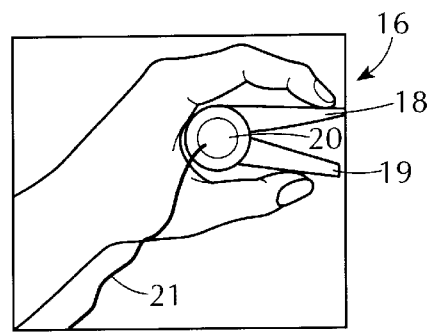
FIG. 3 illustrates a pain rating device in accordance with the invention.

Referring to FIG. 3, the pain rating device 16 may be constructed as a potentiometer having a pair of handles 18, 19 pivotally mounted on a common pivot 20 to provide an output voltage over a line 21 to the computer 15 which is proportional to the distance between the two handles 18, 19. The handles 18, 19 are fixed to the subject's index finger and thumb and the subject is instructed to open or close these two fingers in relation to his/her pain perception, where maximum opening of the fingers signals maximum pain perception and touching the two fingers signals no pain at all.

Figure 4:
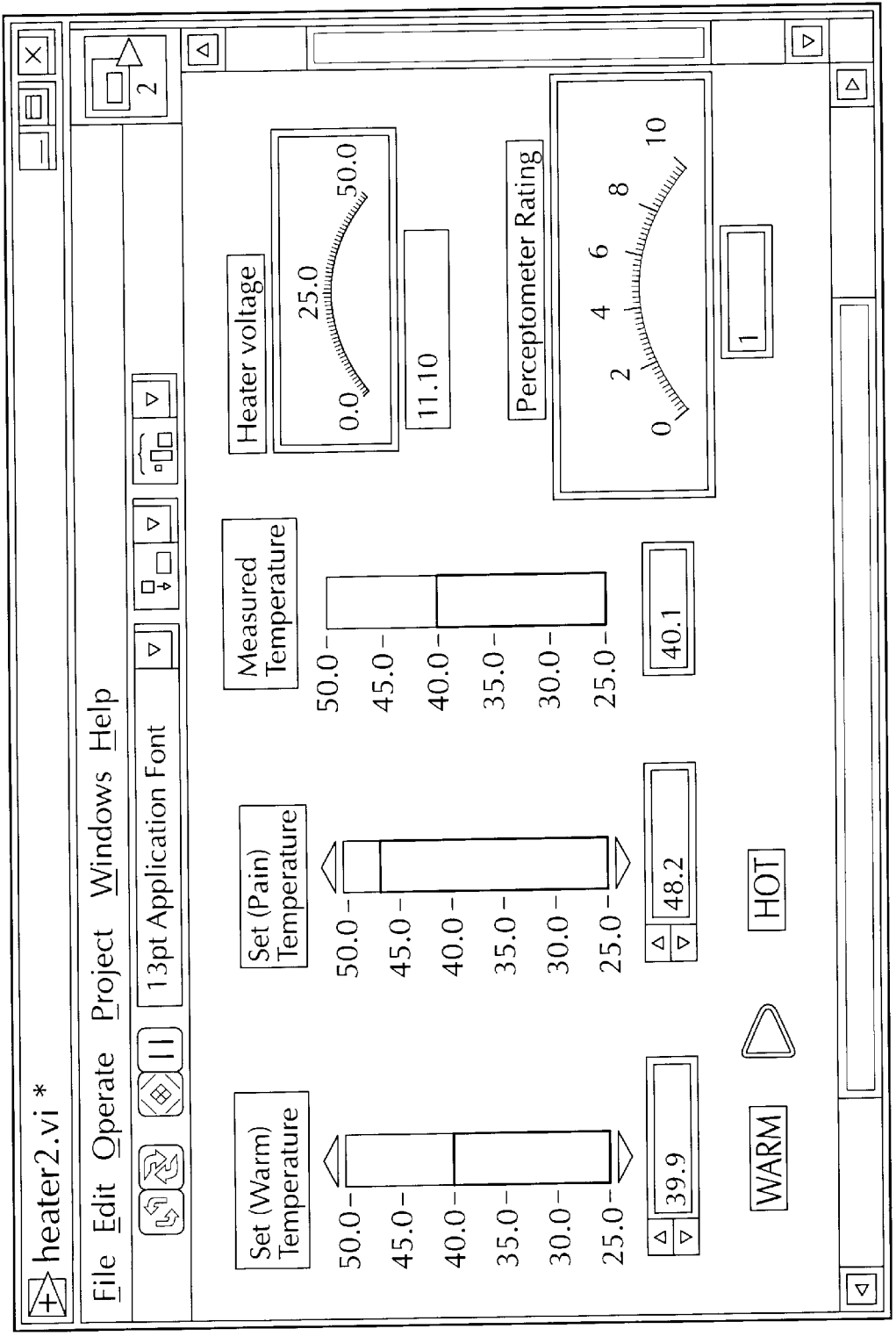
FIG. 4 illustrates a computer interface for controlling a thermal stimulus and monitoring a subject's response in a functional MRI scan.

Referring to FIG. 4, the computer 15 may be constructed and programmed as an interface for controlling noxious thermal stimulus and monitoring the subject's response in a functional MR scan. In this embodiment, the temperature of a thermode is varied between a warm and a hot painful state as a function of MR image number. The subjects response is simultaneously displayed and logged using the pain rating device 16.

As shown in FIG. 4, by way of example, the computer 15 may have a display which includes two temperature settings that control the stimulus and no-stimulus temperatures, a reading of the actual skin temperature, and the perceptometer ratings both of which are updated with every new brain image collection based on the trigger signals 17.

Figure 5:
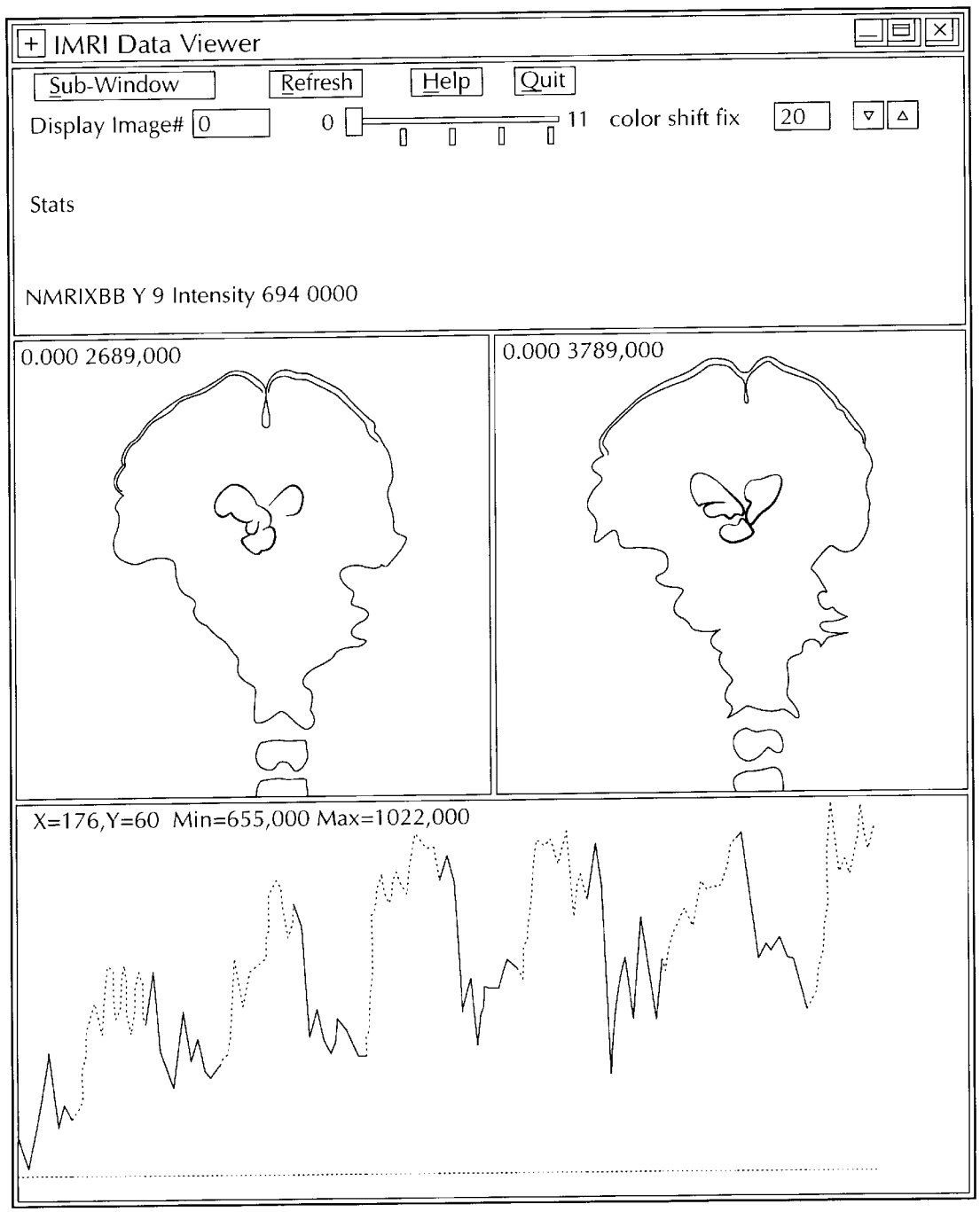
FIG. 5 illustrates a plot of an activated pain region value versus time in accordance with the invention.

Referring to FIG. 5, the computer 11 may have a display which plots an activated region's pixel value versus time wherein black tracings indicate periods of control while lighter portions of tracing correspond to stimulus periods. Alternatively, the black tracings may correspond to periods where the "perceptometer" was at a large value and the lighter portions of tracing correspond to minimal displacement of the "perceptometer". Such a display may shows regions of the brain that are correlated with the perception. Not shown in the figure are software that automatically delineates these areas by statistically comparing all brain regions with the "perceptometer" output. The final brain map generated from such an analysis would show the brain profile for the corresponding pain perception objectively.

The variable painful stimulus may be applied to the subject from an external source as described above or may be applied through external manipulation of the patient such as by raising, lowering or twisting of a leg in the chronic back pain patient.

The technique allows fluctuations in the pain perception caused by external manipulation or spontaneous patient pain variations to be used to identify areas in the brain that are correlated with this perception.

The data analysis computer 13 outputs a log file of pain quantity as a function of time referenced to time points where individual functional image data collection has occurred. This "perception" recording is then used as a reference function to temporally analyze the series of images 12 obtained with the sequence of multiple images spanning a distribution of slice locations. Identification of areas known to be involved with pain perception are graded based on an "activation index", combining the properties of volume of brain tissue as well as the intensity of the activation. Analysis can be of a variety of statistical methods, e.g. Student's t test, z scores, correlation functions, ROC (receiver operator curves) or SPM96 (Statistical Parameter Maps 96: a shareware available on the web for public use).

Research has been carried out on a General Electric Signa clinical MR scanner equipped with echo planar (EPI) capabilities, having additional EPI hardware supplied by Advanced NMR Inc. and by General Electric. Typical imaging parameters are as follows: gradient echo EPI scan with a 128×128 resolution and a 6 mm slice thickness, TR 3500, TE 60, 8 slice locations in either the coronal, axial or oblique planes. Images or unreconstructed data are transferred via computer network to other faster computers running the Unix operating system (AlphaPC165LX or SUN UltraSparc) for reconstruction and data analysis. C-programs were written to compute correlation maps or Student's t-maps or most recently ROC maps. Image pixels displaying activation are further tested by a cluster filter and then passed through a smoothing filter. Additional programs were written to overlay the results of these statistical analyses on higher quality anatomical MR images, yielding attractive and easily interpreted color overlay images. Activation index was computed from the product of pixel statistical significance and total number of pixels activated.

Passing electrical monitoring and stimulus control wires into the electrically shielded MR scanner room required the construction of special radio frequency (r.f.) filters. These filters prevent spurious signals from degrading MR images. Waveguides were installed in the walls of the scan room to permit these electrical cables to penetrate the electrically conductive walls. Other stimulus apparatus relied on pneumatic operated and hot water thermostated devices. In all measurements, a TTL signal from the MR scanner host computer was used to trigger and synchronize the application of stimulus to the subject as well as synchronizing the subject's pain perception from the perceptometer with the collection of individual images. A Pentium 133 computer running Windows95 operating system and National Instruments Labview program with a LabPC+ interface card was found to be a convenient way to control the stimulus process. Thermodes were constructed from electrically heated metal surfaces with an integral temperature monitoring and control circuit.

Since this functional brain mapping technology is very new, calibration studies are necessary to differentiate between various chronic pain states. In these measurements, subjects suffering from chronic pain, e.g. chronic back pain would be evaluated for the presence and severity of perceived pain using the technology embodied herein. If the pain involves the lower spinal segments, then movement of a leg is used to exacerbate the pain while monitoring the blood flow changes in brain cortex using fMRI techniques. The subject continuously rates his pain via the pain rating device 16, e.g. a finger spanning device, as shown in FIG. 3, where a larger separation of fingers indicates severe pain while a smaller separation a lesser degree of pain. As illustrated, the spring biased arms 18, 19 are pivotally mounted about the common pivot 20 for movement from a relaxed position (as shown) towards a stressed position in response to a digitally applied force from a subject to indicate a level of discomfort. The relative positions of the arms 18, 19 are electrically indicated and a corresponding signal is emitted through the line 21 to the computer 15 (see FIG. 1). The value of finger angle is logged in the computer 15 as a function of when images are taken during a scan in the imaging device 10.

A scanning session might last 7 minutes, followed by a control scan where only the spanning device 16 is manipulated to act as a control for the sensorimotor activity in the pain quantification scans. The brain activity pattern can be verified by repeating the procedure following the injection of a local anesthetic to the appropriate spinal segments. After a sufficient experience with a population of back pain patients, the specific calibrated brain activity profiles could be used as a template to compare and categorize other subjects with similar conditions.

By way of example, a population of back pain patients may be tested to obtain corresponding images of brain activity for corresponding pain ratings for use as an aggregate value or template for comparison with other patients with similar conditions. Once the templates have been established, the results obtained for a given patient can then be compared with the template. For example, if a patient provides a pain rating of high value for a given pain inducement, the corresponding brain image should fall within an expected range suggested by the template. If the brain activity pattern deviates from that which would be indicated by the template, this may be an indication of a fraudulent rating by the patient.

A similar protocol could be used to categorize and evaluate chronic headache patients. Here, however, the headache pain would be modulated by existing or external factors, including analgesics or other drugs. The functional MRI scans would be recorded over a longer period of time, e.g. 45 minutes. The extremes in high and low pain states could be identified and used as the input for the analysis of cortical blood flow changes involved with this process.

In many chronic pain diseases, temporal summation properties of pain are abnormal. An example would be a patient suffering from fibromyalgia where their temporal summation of pain is exaggerated. Repetitive thermal or mechanical painful stimuli in this population progress from non-painful to intolerably painful states much faster than in normal subjects. This perceptometer referenced scanning and analysis technique would be used to characterize their cortical pain patterns.

Subjects with phantom limb pain and other abnormal referred pain would constitute yet another application for this technology. The population would be screened to identify the cortical areas involved with their perceptions. Manipulation of the amputation site will often result in pain perceived in the phantom limb. These measurements would be rated with the perceptometer and compared to the same manipulation on the ipsilateral unaffected limb.

In all these examples and similar cases, the procedures can be used for verifying the presence and extent of the claimed pain and monitoring the efficacy of therapeutic procedures in ameliorating the pain state.

The above techniques may also be used to monitor the perception of pain without any additional manipulation. For example, a back pain patient may be placed in the imaging device with instructions to use the rating device 16 to indicate spontaneous changes in pain. The subsequent image sequence of brain responses correlated to the subject-perceived level of discomfort can thus be used to identify the brain regions involved in the pain perception.

Thus, the invention provides a technique in which an fMRI exam is combined with a pain modulation technique and pain rating recording technique. Examples of modulation of pain includes the repetitive mechanical manipulation of the subject by external mechanical control devices during the scan, short duration drug modulation techniques (including local anesthetic blocks), and chemical, thermal, electrical and mechanical exacerbation of existing pain. Another related modulation method includes painful stimuli that manipulate the temporal summation properties of pain perception.

One specific example is the mechanical movement of the foot in a patient with chronic back pain while the subject is scanned by fMRI and indicating the changes in pain intensity with the perceptometer during the scan. The procedure is then repeated immediately following injection of a local anesthetic block in the dorsal root entry zone of the spinal cord. Another example is the mechanical stimulation of a body part in a patient with spinal cord injury to evoke the perception of a referred pain while the patient is being scanned and is reporting with the "perceptometer". In the latter case, the subject is then also scanned while the referred site is stimulated painfully (e.g. with either a mechanical or thermal stimulus), or following an anesthetic block in the region evoking the referred pain.

In addition to the pain imaging sessions, control sessions would be run to eliminate factors unrelated to the pain, i.e. the motor and somatosensory activities that are necessarily introduced as a result of using the perceptometer. The resultant control functional brain images are used to correct the pain images obtained with the perceptometer thereby isolating the pain responses.

The method finds immediate application using functional MRI as a monitoring modality, but would also work with CT, EEG, CEP, near IRS, MEG and other yet undiscovered or undisclosed imaging modalities.

The invention provides a technique which may be used in evaluating the presence of pain and the severity. The technique may also be used to monitor drug efficacy in pain relief and in differentiating between different types of chronic pain. The wide availability of MR scanning instruments makes the technique of wide practical use and the use of higher performance gradient hardware and higher static magnetic fields in current MR research sites increases the sensitivity of this technology.

The invention is particularly useful in evaluating the level of pain in a patient having an affliction such as lower back pain in order to determine the treatment and/or medication to be applied to relief the pain.

The invention also provides a tool which may be used, for example, by workmen's compensation boards, insurance companies and doctors to relate a patient's perceived level of pain with a template of brain activity which should be expected for the rated level of pain. In the event that the brain activity deviates from that which would be expected from the aggregate value or template, this may well be an indication of a fraudulent rating by the patient. Thus, insurance carriers may be able to screen for valid claims as well as fraudulent claims in an objective manner not previously available.

What is claimed is:

1. An assembly for objectively measuring pain, said assembly comprising
    an imaging device for recording and imaging a sequence of brain responses of a subject over a time period and for emitting a trigger signal in response to each imaged brain response;
    a subject controlled pain rating device for emitting a signal corresponding to a subject-perceived level of discomfort of the subject; and
    a computer interface for correlating each of the sequence of brain responses to said signal corresponding to levels of discomfort in dependence on said trigger signals.

2. An assembly as set forth in claim 1 wherein said imaging device is a functional magnetic resonance imaging device.

3. An assembly as set forth in claim 2 wherein said pain rating device includes a pair of spring biased pivotally mounted arms for movement from a relaxed position towards a stressed position in response to a digitally applied force from the subject to indicate a level of discomfort.

4. An assembly as set forth in claim 1 which further comprises means for applying a variable pain-inducing stimulus to the subject over said time period and said imaging device is a functional magnetic resonance imaging device.

5. An assembly for measuring changes in pain, said assembly comprising an imaging device for recording and imaging a sequence of brain images of a subject over a time period and emitting a trigger signal in response to each image;

a first computer for collecting the sequence of brain images from said imaging device and emitting information corresponding thereto;

first means for applying a variable painful stimulus to the subject during said time period;

a pain rating device for indicating levels of discomfort of the subject to said variable painful stimulus over said time period;

a second computer operatively connected to said first means for controlling said first means to vary said stimulus at selected times during said time period and operatively connected to said pain rating device to record changes in the levels of discomfort and to emit information corresponding thereto and connected to said imaging device to receive said trigger signals; and a data analysis computer for receiving said information emitted from said first computer and said information emitted from said second computer to produce a record correlating changes in said brain images in response to changes in said stimulus relative to indicated levels of discomfort.

6. An assembly as set forth in claim 5 wherein said imaging device is a functional magnetic resonance imaging device.

7. An assembly as set forth in claim 5 wherein said pain rating device includes a pair of spring biased pivotally mounted arms for movement from a relaxed position towards a stressed position in response to a digitally applied force from the subject to indicate a level of discomfort.

8. An assembly as set forth in claim 5 wherein said first means applied a thermal stimulus to the subject.

9. A method of objectively measuring pain in a subject, said method comprising the steps of applying a variable painful stimulus to a subject in a time dependent manner;

objectively imaging brain responses of the subject during application of said stimulus;

recording subjective indications of the level of discomfort of the subject during application of said stimulus; and correlating said subjective indications of the level of discomfort with said objectively imaged brain responses to characterize the brain's representation of the pain associated with said stimulus.

10. A method of objectively measuring pain in a subject, said method comprising the steps of subjecting a subject to a variable pain over a period of time;

objectively imaging brain responses of the subject during said period of time;

recording subjective indications of the level of discomfort of the subject during said time period; and correlating said subjective indications of the level of discomfort with said objectively imaged brain responses to characterize the brain's representation of the pain.

11. A method as set forth in claim 10 wherein said step of subjecting a subject to a variable pain includes external manipulation of the subject.

12. A method as set forth in claim 10 wherein said step of subjecting a subject to a variable pain includes application of an external stimulus.

13. A method as set forth in claim 12 wherein the external stimulus is a thermal stimulus.

14. A method as set forth in claim 10 wherein the brain responses are imaged with a magnetic resonance imaging device.

15. A method of identifying brain regions involved in pain perception comprising the steps of objectively imaging brain responses of a subject over a period of time to obtain a sequence of brain images;

recording subjective indications of the level of pain of the subject during said period of time; and correlating said subjective indications with said sequence of brain images to identify brain regions corresponding to a subjective level of pain.

* * * * *